United States Patent [19]
Godlewski

[11] Patent Number: 5,350,101
[45] Date of Patent: Sep. 27, 1994

[54] DEVICE FOR ADVANCING A ROTATABLE TUBE

[75] Inventor: Peter P. Godlewski, San Carlos, Calif.

[73] Assignee: Interventional Technologies Inc., San Diego, Calif.

[21] Appl. No.: 17,529

[22] Filed: Feb. 16, 1993

Related U.S. Application Data

[63] Continuation-in-part of Ser. No. 616,983, Nov. 20, 1990, abandoned.

[51] Int. Cl.$^5$ ............................................. B65H 20/00
[52] U.S. Cl. .................................. 226/129; 226/161; 226/162; 226/165
[58] Field of Search ............... 226/128, 129, 158, 161, 226/162, 165, 166, 167

[56] References Cited

U.S. PATENT DOCUMENTS

| | | | |
|---|---|---|---|
| 222,618 | 12/1879 | Woodruff | 226/128 |
| 284,501 | 9/1983 | Smith | 226/128 |
| 300,943 | 6/1884 | Booth | 226/128 |
| 1,951,545 | 3/1934 | Carson | 226/128 |
| 2,003,152 | 5/1935 | Lange et al. | 29/59 |
| 2,035,354 | 3/1936 | Hamersveld | 29/59 |
| 2,388,594 | 11/1945 | Bogart | 226/164 |
| 2,625,934 | 1/1953 | Halliday | 128/303 |
| 2,801,608 | 8/1957 | Peck | 118/108 |
| 2,832,603 | 4/1958 | Cracchiolo | 226/166 |
| 3,298,666 | 1/1967 | Prange | 254/105 |
| 3,335,930 | 8/1967 | Peffer | 226/165 |
| 3,404,822 | 10/1968 | Green | 226/158 |
| 3,580,448 | 5/1971 | Cagle, Sr. | 226/127 |
| 3,896,982 | 7/1975 | Redman | 226/164 |
| 3,999,697 | 12/1976 | Hill, Jr. | 226/128 |
| 4,000,891 | 1/1977 | Klafka | 271/8 |
| 4,057,186 | 11/1977 | Hedger | 226/127 |
| 4,139,135 | 2/1979 | Krupenik | 226/166 |
| 4,266,109 | 5/1981 | Ciolkevich | 219/10.57 |
| 4,326,520 | 4/1982 | Alley | 128/214.4 |
| 4,336,947 | 6/1982 | Franklin | 279/46 |
| 4,378,076 | 3/1983 | Stirnweiss | 222/146 |
| 4,615,472 | 1/1986 | Nash | 226/127 |

Primary Examiner—Daniel P. Stodola
Assistant Examiner—Michael R. Mansen
Attorney, Agent, or Firm—Nydegger & Associates

[57] ABSTRACT

A stock feeder has a housing for supporting both the stock and an advancer which coaxially extends through the housing and is formed as a collet which, when clamped, grips the stock and holds the advancer in a fixed relationship with the stock. At the extreme distal end of the advancer the collet is formed with a radially extending lip, and proximal to the collet the advancer is formed with a radially extending ring. A chuck which is formed with a radial groove slidingly surrounds the collet and is movable relative to the advancer. Specifically, the chuck can be moved on the collet between a first position wherein the chuck clamps the collet onto the stock and a second position wherein the collet is released to allow a sliding movement of the stock through the advancer. In either collet configuration, the stock may be rotated. An actuator is engaged with the groove on the chuck and is manipulable to move the chuck between the first and second positions. An abutment formed with a hole for receiving the tube therethrough is held at a distance distal or forward from the housing by an extension arm which interconnects the housing and the abutment. Additionally, a cylindrical-shaped spacer is positioned around the stock between the chuck and the abutment.

11 Claims, 2 Drawing Sheets

DEVICE FOR ADVANCING A ROTATABLE TUBE

This is a continuation in part application of co-pending application Ser. No. 07/616,983, filed on Nov. 20, 1990 and entitled Tube Feeder now abandoned.

FIELD OF THE INVENTION

The present invention relates generally to stock feeder devices. More specifically, the present invention relates to devices which can be manipulated to alternately grip and release a section of stock to advance or retract the stock even as the stock is being rotated. The present invention is particularly, though not exclusively, useful for advancing a tube catheter into an artery of a living being.

BACKGROUND OF THE INVENTION

A wide variety of tube feeding devices have been introduced which grip and then feed stock into processing machinery for further manipulation of the stock. Such devices are preferred over manual insertion of stock for several reasons. First, when stock is to be fed into operating machinery, it is generally safer to feed the stock into the machine using a mechanical device, rather than feeding the stock into the machine by hand. An example of such a device is the apparatus described in U.S. Pat. No. 2,003,152, which discloses a stock feeder for gripping and then feeding the stock into a turret lathe. Second, it is easier to feed precise lengths of stock into processing machinery, if required, when a mechanical apparatus is used to feed the stock. An example of such a device is that disclosed in U.S. Pat. No. 2,035,354.

In addition to the industrial applications mentioned above, stock feeding devices are also used in certain modern surgical techniques, such as the now well-known angioplasty surgery. These techniques typically require the insertion of a significant length of stock, or tubing, into an artery of the patient. For example, U.S. Pat. No. 4,615,472 discloses a catheter placement device for inserting a catheter into an artery for subsequent removal of plaque from the artery using well-known angioplasty techniques.

In the applications described above, it is sometimes necessary that the stock be rotated as it is fed into the processing machine or artery. For example, in the case of atherectomy surgery applications, several well-known devices are used to mechanically cut away arterial plaque by means of a rotating cutter at the end of a tube which has been inserted into the artery. Thus, the stock feeding devices used in such applications must be capable of gripping a rotating length of stock and then advancing (or retracting) the stock as required.

Accordingly, it is an object of the present invention to provide a stock feeder device which is relatively light weight and easy to use. It is another object of the present invention to provide a stock feeder device which can insert relatively precise lengths of stock into a channel. Still another object of the present invention is to provide a stock feeding device which can incrementally advance a piece of stock while it is being rotated. Another object of the present invention is to provide a stock feeder device which can grip and advance stock which has a wide range of diameters. Yet another object of the present invention is to provide a stock feeder device which is cost-effective to manufacture and which is capable of withstanding appropriate sterilization procedures.

SUMMARY OF THE INVENTION

A tube feeder device includes a housing for supporting both the tube and a cylindrically-shaped advancer which slidingly surrounds a portion of the tube. The advancer itself is slidingly mounted on the housing and the distal end of the advancer extends outwardly from the housing. A tapered collet is formed on the distal end of the advancer which, when clamped, grips the tube and holds the advancer in a fixed relationship with the tube. At the extreme distal end of the collet, the collet is formed with a radially extending lip, and on the main portion of the advancer proximal to the collet, the advancer is formed with a radially extending ring. A chuck slidingly surrounds the collet and is movable relative to the advancer. Specifically, the chuck can be moved relative to the advancer between a first position, wherein the chuck clamps the collet onto the tube, and a second position, wherein the collet is released to allow a sliding movement of the tube through the advancer. An actuator is slidingly engaged with a groove that is formed radially on the chuck and is manipulable to move the chuck between the first and second positions.

An abutment formed with a hole for receiving the tube is held at a distance distal or forward from the housing by an extension arm which interconnects the housing and the abutment. Additionally, a cylindrically-shaped spacer is positioned around the tube between the abutment and the collet. The spacer may be formed on the abutment or may be slidably disposed around the tube.

In the operation of the tube feeder, the actuator is first moved in the rearward, or proximal, direction, i.e. toward the housing, in order to clamp the collet onto the tube. Specifically, this proximal movement of the chuck draws the advancer into the housing until the ring on the advancer contacts the front plate of the housing to prevent any further relative movement between the housing and the advancer. An additional rearward or proximal movement of the actuator, which remains engaged with the chuck, then causes the chuck to move into its first position relative to the advancer and to clamp the collet onto the tube. Importantly, the angle of the taper of the collet relative to the collet's axis induces sufficient frictional force between the chuck and the collet when the chuck is in the first position to securely hold the chuck onto the clamped collet.

When the collet is clamped onto the tube, any distal or forward movement of the actuator causes the tube to be advanced together with the actuator. This forward movement may be continued and controlled by manipulation of the actuator until the spacer becomes wedged between the abutment and the collet. At this point, the collet can be advanced no further and an additional forward or distal movement of the actuator will move the chuck into its second position relative to the advancer to thereby release the grip of the collet on the tube. Importantly, because the actuator is slidingly engaged with the collet, it happens that the tube, the advancer, and the collet may be independently or collectively rotated relative to other parts of the device. Consequently, with the collet of the advancer clamped onto the tube, a rotating tube may be advanced using this device.

When the collet is released from the tube, the tube can be held stationary and the actuator can be manipulated to move the advancer in a rearward or proximal direction. This rearward movement of the advancer may be continued until the ring on the advancer again makes contact with the front plate of the housing and the chuck is moved into its first position, as described above. The entire process can then be repeated as necessary.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF THE PREFERRED EMBODIMENT

For purposes of disclosure, a medical application for the device of the present invention is described. This is for illustration only and is not intended to be limiting. Indeed, any application wherein it is desirable to intermittently advance rotatable stock having a wide range of outer diameters would be appropriate for the present invention.

Figure 1:
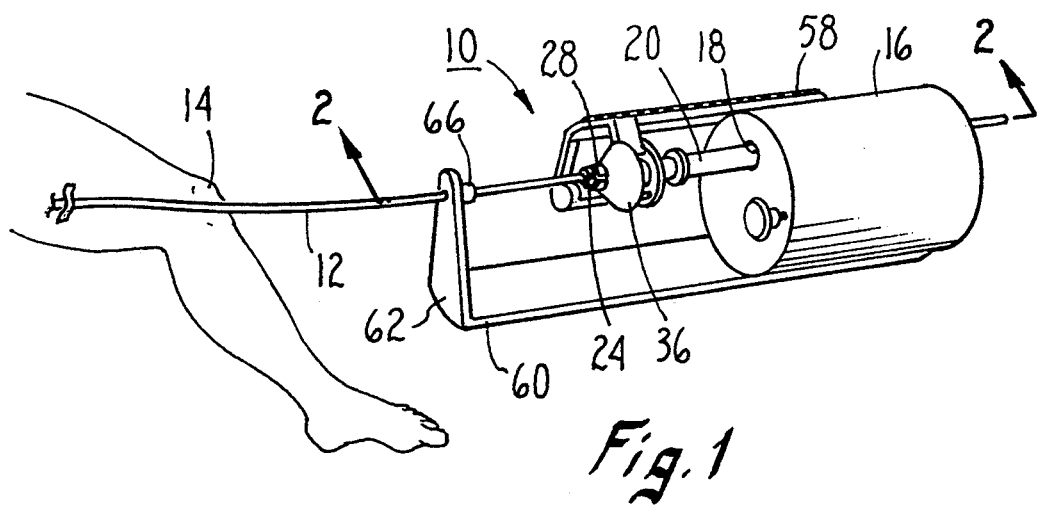
FIG. 1 is a perspective view of the novel tube feeder device of the present invention in one intended environment.
Figure 2:
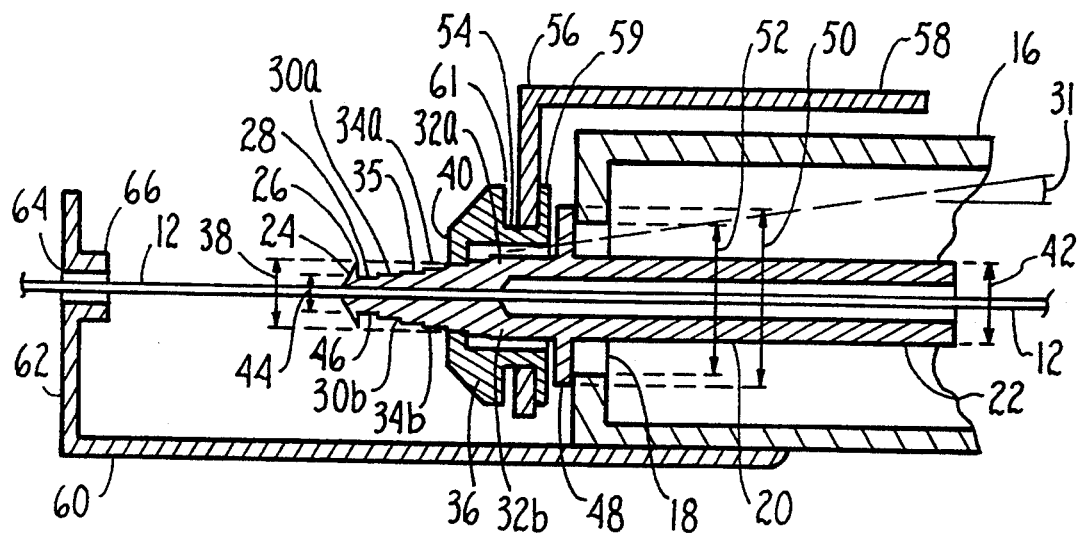
FIG. 2 is a side cross-sectional view of the novel tube feeder device of the present invention as seen along the line 2—2 in FIG. 1 with the collet shown in its retracted position gripping the tube.

Referring initially to FIG. 1, a tube feeder device, generally designated 10, is seen operatively connected with a catheter tube 12 for inserting the tube 12 into a patient 14 during a medical procedure. The details of device 10, however, may be best seen by cross-referencing FIGS. 1 and 2. There, it may be seen that device 10 includes an elongated hollow housing 16 which has an opening 18 for radially supporting an advancer 20. Advancer 20, as best seen in FIG. 2, is formed with a proximal end 22 and a distal end 24. The tube 12 is coaxially disposed through advancer 20, and, as seen in FIG. 2, distal end 24 of advancer 20 has a lip 26 and a collet 28, which both surround tube 12. As is typical for such a structure, the collet 28 may include a suitable plurality of radially spaced resilient collet figures or segments 30a, 30b.

Figure 3:
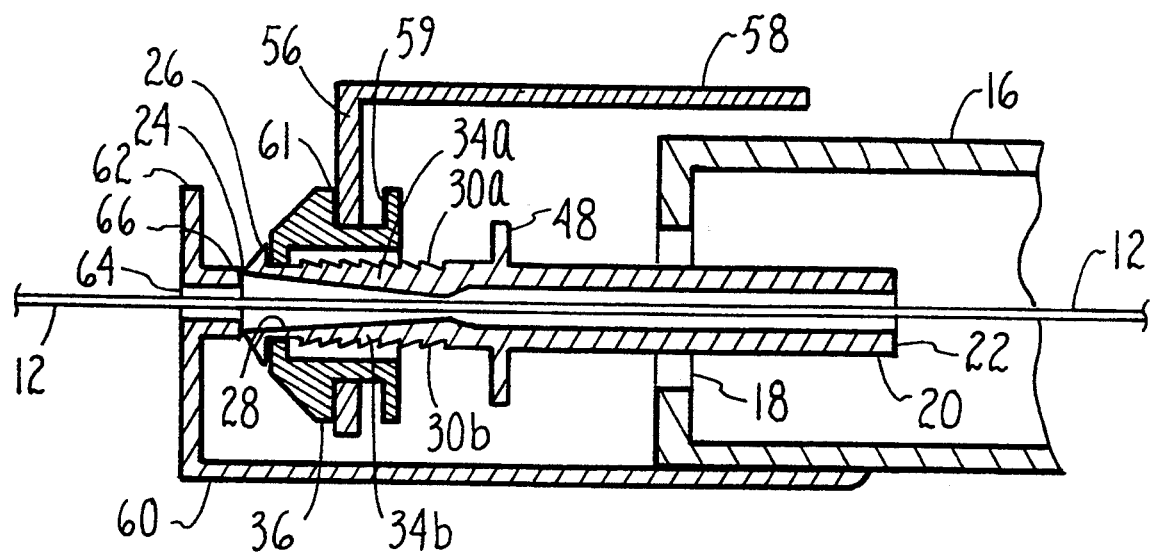
FIG. 3 is a cross-sectional view of the novel tube feeder device of the present invention as seen along the line 2—2 in FIG. 1, with the collet shown in its forward position releasing the tube.

In the embodiment shown, collet 28 includes four such collet segments 30 which have substantially identical configurations (two of these segments, i.e. segments 30a, b are shown in FIG. 2). As best seen in FIG. 2, each collet segment 30a, b has a substantially linear portion 32a, b and a tapered portion 34a, b, respectively. Importantly, the angle of taper 31 of the portions 34a, b relative to the longitudinal axis defined by tube 12 is established to be in the range 5° to 15°. As the skilled artisan will appreciate, because collet segments 30 are resilient and are radially spaced from each other, the segments 30 may be compressed inwardly around tube 12 into a position which allows the segments 30 to grip tube 12. Due to the leverage obtained by the above disclosed configuration the segments 30 are capable of gripping tube 12 with a substantial force. Further, due to the flexibility of each segments 30 collet 28 is capable of gripping various sizes of stock with substantially equal force, the gripping force being relatively independent of the diameter of the particular stock. On the other hand, the collet segments 30 are normally resiliently biased outward to their position as shown in FIG. 3, wherein no contact between the collet segments 30 and tube 12 is established.

FIGS. 1 and 2 also show a substantially rigid chuck 36 which surrounds collet 28 and which is axially movable relative to advancer 20. As shown in FIG. 2, each tapered portion 34a, b can be formed with steps 35 to provide an audible indication of chuck 36 sliding relative to collet 28 to indicate that chuck 36 has gripped collet 28. As will be appreciated by those skilled in the art, the steps 35 of collet 28 are shown greatly exaggerated in size. For purposes of providing the audible indication, steps 35 may be extremely small, e.g. in the order of one-half of one one-thousandth of an inch (0.0005 in.). The material used for collet 28 and chuck 36 can be plastic, metal or any other similar material. These materials allow localized deformation of the steps 35, which allows chuck 36 to move over steps 35.

Figure 4:
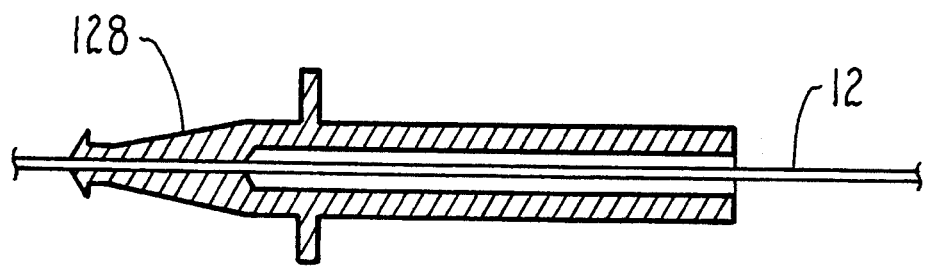
FIG. 4 is an alternate embodiment of the collet member.

It is to be noted that as is shown in FIG. 4, the collet need not include the steps for proper functioning of the tube feeder of the present invention. It is to be appreciated that using the collet 128 as shown in FIG. 4 would not produce the audible indication produced by collet 28 in FIG. 3.

Referring again to FIGS. 1 and 2, chuck 36 is movable on advancer 20 between lip 26 and a point on collet 28 that is intermediate tapered portions 34a, b. It is therefore to be appreciated that inside diameter 38 of end 40 of chuck 36 is marginally smaller than outside diameter 42 of advancer 20. On the other hand, inside diameter 38 is marginally larger than the outside diameter 44 of the end 46 of collet 28.

In addition to the collet 28 structure disclosed above, advancer 20 is also formed with a ring 48 which circumscribes the advancer 20. It is to be appreciated that diameter 50 of ring 48 is larger than diameter 52 of opening 18. This in turn causes ring 48 to abut housing 16 when advancer 20 is moved to its retracted position shown in FIG. 2. FIG. 2 also shows a radial groove 54 which is formed on chuck 36 for the purpose of receiving an extension 56 of an actuator 58. More specifically, though extension 56 is slidingly received in groove 54 of chuck 36 and thus will not inhibit any rotation of chuck 36, extension 56 can be urged against either side 59 or side 61 of groove 54. Accordingly, actuator 58 is manipulable to urge chuck 36 to the left or right in FIG. 2.

Still referring to FIGS. 1 and 2, device 10 is shown further having an extension arm 60 which has an abutment 62 formed on arm 60. More particularly, extension arm 60 is fixedly attached to or formed integrally with housing 16. As shown in FIG. 2, abutment 62 is formed with an opening 64 for supporting tube 12. Finally, a cylindrical-shaped spacer 66 is shown integrally formed on abutment 62. It is to be understood that spacer 66 may alternatively be slidably positioned around tube 12 between abutment 62 and lip 26 or integrally formed on distal end 24 of advancer 20.

With regard to the above-disclosed structure, it is to be understood that the materials of tube feeder device 10 are preferably composed of a strong, yet lightweight, material such as hard plastic although some metals may also be usable. Furthermore, the materials of device 10 are preferably capable of withstanding any sterilization procedures which may be necessary for certain medical applications of device 10.

OPERATION

In the operation of tube feeder device 10, cross-reference is made to FIGS. 2 and 3. Tube 12 is first inserted through housing 16, advancer 20, spacer 66, and opening 64 of abutment 62. Then, the actuator 58 is moved in the proximal direction, i.e., toward housing 16. This motion of actuator 58 also pulls chuck 36 and, hence, advancer 20 toward housing 16 until ring 48 of advancer 20 contacts housing 16.

As shown in FIG. 2, further proximal motion of actuator 58 will not move advancer 20 but will instead cause chuck 36 to slide along the tapered portions 34 of collet segments 30 to thereby clamp collet 28 around tube 12. More specifically, as chuck 36 slides along collet 28, resilient collet segments 30 are thereby urged against tube 12 to grip tube 12, as shown in FIG. 2. The frictional force between chuck 36 and tapered portions 34 of collet 28 which results from urging chuck 36 proximally along tapered portions 34 fixedly engages chuck 36 around collet 28. Chuck 36 in turn holds collet 28 in the clamped position of collet 28 shown in FIG. 2. It may now be appreciated that the angle 31 of the taper of tapered portions 34 is established to provide frictional force between chuck 36 and collet 28 which is sufficient to hold chuck 36 and collet 28 in their clamped configuration. Importantly, tube 12 may be rotated by a rotating motor (not shown) as tube 12 extends through tube feeder device 10, even when collet 28 clamps tube 12 as disclosed above.

Once collet 28 has gripped tube 12, any distal movement of actuator 58 (i.e., toward the left in FIGS. 1 and 2) causes tube 12 to be advanced along with actuator 58. Alternatively, actuator 58 could be manipulated to retract tube 12 (i.e., move tube 12 to the right in FIGS. 1 and 2) if desired by the operator of device 10. This proximal motion will, of course, be limited by the contact of ring 48 against housing 16. In the case of distal motion of actuator 58 (and, hence, tube 12), distal motion may continue until it is eventually limited by spacer 66 becoming wedged between abutment 62 and lip 26 of collet 28, as shown in FIG. 3. Further distal motion of actuator 58 will cause chuck 36 to slide relative to now-stationary collet 28 toward distal end 24 of advancer 20. Chuck 36 will continue to slide along collet 28 until further motion of chuck 36 is prevented by its contact with lip 26 of collet 28. With this motion, the grip of collet 28 on tube 12 is released. More specifically, as chuck 36 slides distally along tapered portions 34a and b of collet segments 30a, and b (i.e., toward the left in FIG. 3), collet segments 30a, and b thereby become unconstrained by chuck 36.

Once unconstrained by chuck 36, collet segments 30a, b resiliently retract from tube 12 to their normal, biased position shown in FIG. 3 to release the grip of collet 28 on tube 12. Subsequently, actuator 58 may be manipulated to move the advancer 20 in a proximal direction (i.e., to the right in FIG. 3) while tube 12 remains stationary. As disclosed above, this proximal motion of advancer 20 will eventually be limited when ring 48 of advancer 20 contacts housing 16. Further proximal motion of actuator 58 will accordingly move chuck 36 along collet 28 until chuck 36 has clamped collet 28 onto tube 12, as shown in FIG. 2. The entire process may then be repeated as necessary.

While the particular tube feeder as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

I claim:

1. A device for advancing an elongated piece of stock, which comprises:

a housing;

a collet for radially surrounding a portion of said stock, said collet being movable between a first configuration wherein said collet grips said stock for translation with said stock, and a second configuration wherein said collet releases said stock for independent movement of said collet relative to said stock;

a chuck slidingly surrounding said collet and movable relative thereto between a first position and a second position for respectively moving said collet into said first and second configurations, said chuck being formed with a radial groove;

an actuator having a projection formed perpendicularly thereon for engaging said groove of said chuck;

an elongated advancer having first and second ends, wherein said collet is formed as said first end of said advancer, said second end of said advancer being slidably attached to said housing and said advancer being formed with a ring extending radially outward from said advancer intermediate said first and second ends, said stock slidably and rotatably extending coaxially through said advancer and said housing;

first means attached to said device for limiting the advancing translation of said collet to cause said chuck to move into said second position; and second means distanced from said first means and attached to said device for limiting independent movement of said collet to move said chuck into said first position.

2. A device for advancing stock as recited in claim 1, further comprising an extension arm attached to said housing and extending axially therefrom, said arm being formed with an abutment having a hole for receiving said stock.

3. A device for advancing stock as recited in claim 2, wherein said first means comprises said abutment.

4. A device for advancing stock as recited in claim 2, wherein said collet comprises a distal end and a proximal end, said distal end of said collet being said first end of said advancer, and wherein said distal end of said collet is formed with a radially outwardly extending lip, said collet being axially tapered from its proximal end to its distal end, said lip limiting said advancement of said chuck when said lip contacts said abutment to cause said chuck to advancingly slide relative said collet to move said collet into said second configuration.

5. A device for advancing stock as recited in claim 4, further comprising a spacer having first and second ends and slidingly surrounding said stock intermediate said abutment and said collet for contacting said abutment at said first end of said spacer and contacting said lip at said second end of said spacer to limit said advancing of said collet.

6. A device for advancing stock as recited in claim 1, wherein said second means comprises said housing, said housing being formed to abut said ring to limit movement of said collet toward said housing.

7. A device for advancing stock which comprises:
first means for slidably supporting said stock at a first location on said stock;
second means for slidably supporting said stock at a second location on said stock, said second means being fixedly connected with said first means;
a collet radially disposed around a portion of said stock between said first and second supporting means, said collet being transformable between a first configuration wherein said collet grips said stock and a second configuration wherein said collet releases said stock;
a chuck having a radial groove formed thereon, said chuck slidingly surrounding said collet for movement between a first position and second position for transforming said collet into said first and second configurations; and
an elongated actuator having a protection formed perpendicularly thereon for engaging said groove of said chuck for translating said chuck for selectively contacting said first and second supporting means, to transform said collect into said second and first configurations, respectively.

8. A device for advancing stock as recited in claim 7, wherein said first supporting means comprises a housing and an elongated advancer having distal and proximal ends, said collet being formed as said distal end of said advancer, said proximal end of said advancer extending into said housing, said advancer being formed with a ring radially extending outward from said advancer intermediate said distal and proximal ends for abutting said housing to limit proximal motion of said advancer.

9. A device for advancing stock as recited in claim 8, wherein said first supporting means comprises an extension arm attached to said housing and extending axially therefrom, said arm being formed with an abutment extending perpendicularly therefrom, said abutment having a hole therethrough for establishing a passageway for said stock.

10. A device for advancing stock as recited in claim 9, wherein said collect has a distal end and a proximal end, said distal end of said collet being formed with a radially outwardly extending lip, said collet being axially tapered from its proximal end to its distal end, said lip limiting said advancing of said chuck when said lip contacts said abutment to cause said chuck to advancingly slide relative said collet to move said collet into said second configuration.

11. A device for advancing stock as recited in claim 10, further comprising a spacer having first and second ends and slidingly surrounding said stock intermediate said abutment and said collet for contacting said abutment at said first end of said spacer and contacting said lip at said second end of said spacer to limit said advancing of said collet.

* * * * *